(12) United States Patent
Ernst et al.

(10) Patent No.: US 6,743,954 B2
(45) Date of Patent: Jun. 1, 2004

(54) PROCESS FOR THE PREPARATION OF MESO-ZEAXANTHIN

(75) Inventors: Hansgeorg Ernst, Speyer (DE); Klaus Henrich, Haβloch (DE); Klaus Ditrich, Gönnheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 14 days.

(21) Appl. No.: 10/237,807

(22) Filed: Sep. 10, 2002

(65) Prior Publication Data

US 2003/0092775 A1 May 15, 2003

(30) Foreign Application Priority Data

Sep. 13, 2001 (DE) ......................... 101 45 223

(51) Int. Cl.[7] ............................................. C07C 35/18
(52) U.S. Cl. ..................................................... 568/824
(58) Field of Search ......................................... 568/824

(56) References Cited

U.S. PATENT DOCUMENTS

| | | | |
|---|---|---|---|
| 2,902,515 A | | 9/1959 | Montavon et al. ............ 260/598 |
| 4,153,615 A | * | 5/1979 | Saucy |
| 4,594,456 A | | 6/1986 | Schaefer-Luederssen ... 568/447 |
| 4,952,716 A | * | 8/1990 | Lukac |
| 5,227,507 A | | 7/1993 | Lukac et al. ................. 556/449 |
| 5,523,434 A | | 6/1996 | Burns et al. ................... 554/68 |
| 6,103,940 A | | 8/2000 | Paust et al. .................. 568/823 |
| 6,218,436 B1 | | 4/2001 | Howard et al. .............. 514/725 |

FOREIGN PATENT DOCUMENTS

| | | |
|---|---|---|
| DE | 1046011 | 8/1956 |
| EP | 0 283 979 | 9/1988 |
| EP | 0 834 536 | 4/1998 |
| GB | 1508195 | 4/1978 |
| GB | 1508196 | 4/1978 |
| WO | WO 96/02594 | 2/1996 |

OTHER PUBLICATIONS

H. Mayer "Synthesis of Optically Active Carotenoids and Related Compounds" Pure & Appl. Chem. vol. 51 (1979) pp. 535–564.
Pfander "Synthesis of Carotenoid Glycosylesters and Other Carotenoids" Pure & Appl. Chem. vol. 51 (1979) pp. 565–580.
Pfander et al. "Synthese von (3 R)–β–Citraurin, (3 R)–β–Citraurol unde (3 R)–β–Citraurinin; Aufklärung der Konfinguration von Citrus–Carotinoiden[1])" Helvetica Chimca Acta vol. 63, Fasc. 6 (1980) Nr. 143 pp. 1377–1382, (No translation).
Rüttmann et al. "Synthese von optisch aktiven, natürlichen Carotinoiden und strukturell verwandten Naturprodukten" Helvetica Chimca, Acta vol. 63 Fasc. 6 (1980) Nr. 154 pp. 1456–1462, (No translation).

Soukup et al. Technical Procedures for the Synthesis of Carotenoids and Related Compounds from 6–Oxo–Isophorone: Synthesis of (3 R, 3'R)–Zeaxanthin Helvetica Chimca Acta vol. 73 (1990) pp. 868–873.
Kropf "Enantiomerentrennung (Racematspaltung) von Alkoholen" (1984) pp. 785–796, Houhen–Wayl Method der Organischen Chemie, Part III, (no translation).
Oppolzer et al. "A Short and Efficient Synthesis of (±)–Modhephene by a Stereoelectronically–Controlled Ene–Reaction" Helvetica Chimica Acta vol. 64, Fasc. 7 (1981) Nr. 244 pp. 2489–2491.
Ernst "Wittig Olefination" Carotenoids vol. 2, Synthesis (1996) pp. 78–102.
Buddrus "Dehydrohalogenierunn von Phosphoniumhalogeniden durch epoxide" Chem. Ber. vol. 107 (1974) pp. 2050–2061.
Yamano et al., *J. Chem. Soc., Perkin Trans. 1*, 1998, 2569–2581.
Tode et al., *J. Chem. Soc., Perkin Trans. 1*, 2001, 3338–3345.
Yamano et al., *Chem. Pharm. Bull.*, 49(12), 2001, 1662–1663.
Yamano et al., *Chem. Pharm. Bull.*, 48(12), 2000, 2017–2018.
Yamano et al., *J. Chem. Soc., Perkin Trans. 1*, 1996, 1337–1339.
Krasnobajew et al,. *Helv. Chim. Acta*, vol. 65, Fasc. 5, 1982, Nr. 156, 1590–1601.
Khan et al., *Islamabad J. Sci. 5*, (1–2), 1978, 42–44.

* cited by examiner

*Primary Examiner*—Michael L. Shippen
(74) *Attorney, Agent, or Firm*—Keil & Weinkauf

(57) ABSTRACT

A process for the preparation of optically pure acetylenediols of the formulae R-I and S-I

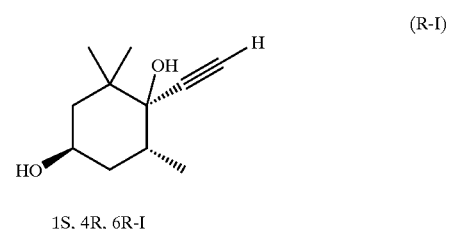

1S, 4R, 6R-I

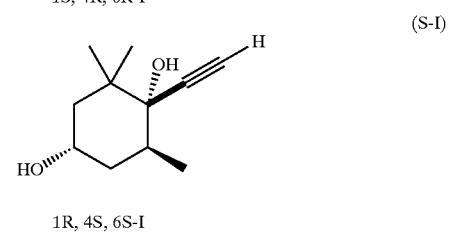

1R, 4S, 6S-I and their further reaction to give meso-zeaxanthin are described.

17 Claims, No Drawings

PROCESS FOR THE PREPARATION OF MESO-ZEAXANTHIN

Process for the preparation of meso-zeaxanthin

The present invention relates to a novel process for the preparation of meso-zeaxanthin. Meso-zeaxanthin is of great importance, inter alia, for the therapy and prophylaxis of age-related macular degeneration (AMD).

Blindness in old age as a result of age-related macular degeneration is an important problem from the epidemiological point of view. More recent investigations show that certain carotenoids can protect the eye effectively from AMD and thus from blindness. The carotenoids which exert this protection function are lutein and zeaxanthin.

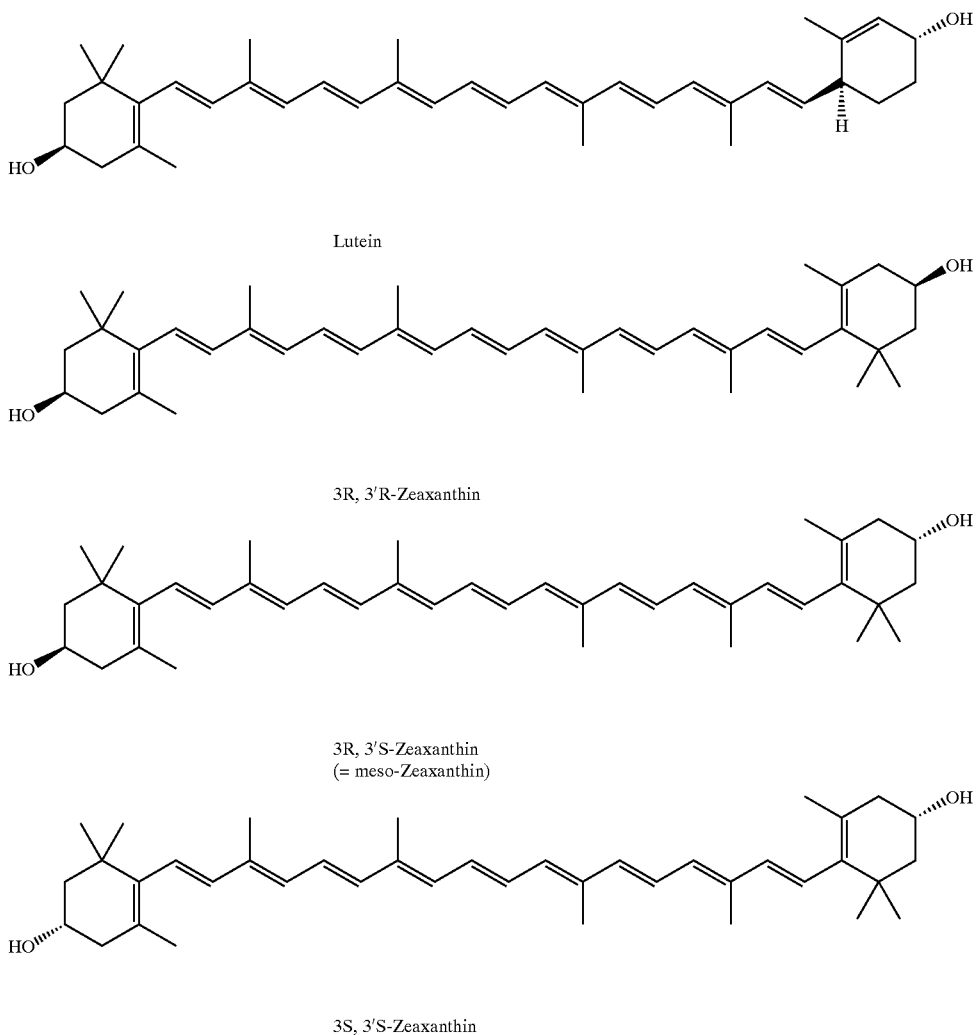

Lutein 3R, 3'R-Zeaxanthin 3R, 3'S-Zeaxanthin
(= meso-Zeaxanthin)

3S, 3'S-Zeaxanthin

Lutein and zeaxanthin can be employed both for prophylaxis and for the treatment of advanced AMD. The administration of meso-zeaxanthin and lutein was described as particularly efficacious (U.S. Pat. No. 6,218,436). meso-Zeaxanthin has to be made available for this therapeutic task. Since isolation from natural sources is excluded, only partial syntheses (isomerization of Lutein) or totally synthetic processes are suitable.

There has been no lack of attempts to convert lutein into meso-zeaxanthin by base-catalyzed isomerization (EP-A-0 834 536; WO 96/02594; U.S. Pat. No. 5,523,434). The processes described here for the isomerization of lutein always lead to mixtures of lutein and meso-zeaxanthin. A uniform product, which is desired for therapeutic purposes, can be obtained from such mixtures only by extremely complicated separation operations, associated with high yield losses.

A multistage total synthesis of meso-zeaxanthin, starting from Safranal, is described in Pure Appl. Chem. 51, 535 f. (1979), Pure Appl. Chem. 51, 565 f. (1979), Helv. Chim. Acta 63, 6, 1377, (1980) and Helv. Chim. Acta 63, 6, 1465, (1980).

The yields of meso-zeaxanthin achieved here are too low for industrial implementation of the synthesis. In order to obtain a uniform final product, on account of the low selectivities of many reaction steps it is necessary to laboriously purify many of the intermediates obtained.

It is therefore an object of the present invention to make available a process for the preparation of meso-zeaxanthin using which the abovementioned disadvantages of the prior art are avoided.

We have found that this object is achieved by a process for the preparation of meso-zeaxanthin,

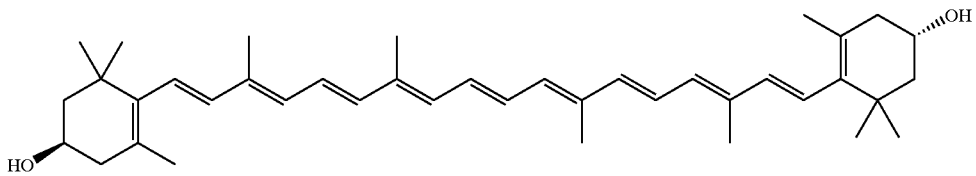

meso Zeaxanthin which comprises a) resolving a racemic mixture of the acetylenediols R-I and S-I (R-I)

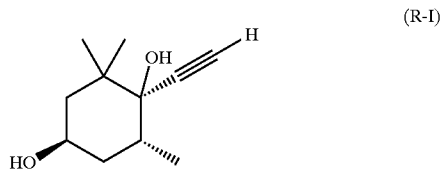

1S, 4R, 6R-I (S-I)

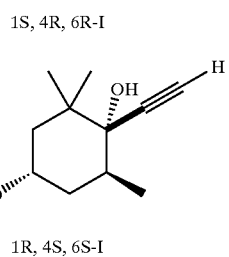

1R, 4S, 6S-I into its antipodes, b) converting the separated antipodes R-I and S-I in each case into the $C_{15}$-phosphonium salts R-II and S-II respectively

R-II

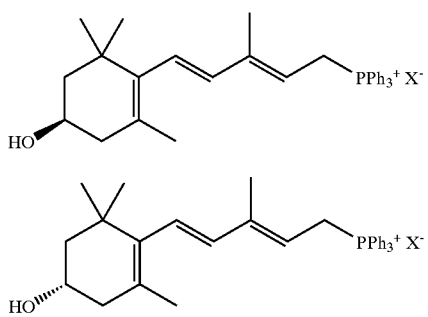

S-II in which Ph is aryl and X is an anion equivalent of an inorganic or organic acid, c) reacting the phosphonium salts R-II or S-II with a $C_{10}$-dial monoacetal of the general formula III,

III

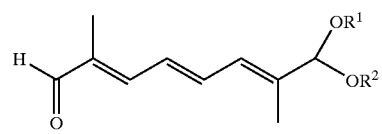

in which the substituents $R^1$ and $R^2$ independently of one another are $C_1$–$C_8$-alkyl or, together with the oxygen atoms and the carbon atom to which they are bonded, can form a 1,3-dioxolane or 1,3-dioxane ring of the following structures

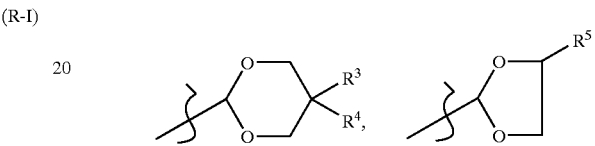

in which $R^3$ and $R^4$ and also $R^5$ in each case independently of one another can be hydrogen or $C_1$–$C_4$-alkyl, in a Wittig reaction to give the $C_{25}$-acetals R-IV or S-IV,

R-IV

S-IV

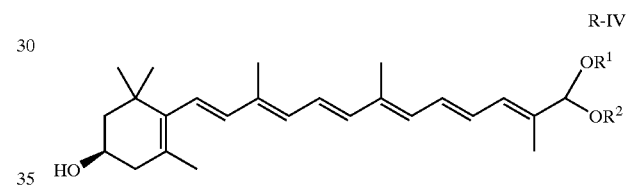

d) converting the $C_{25}$-acetals R-IV or S-IV into the $C_{25}$-aldehydes R-V or S-V

R-V

S-V

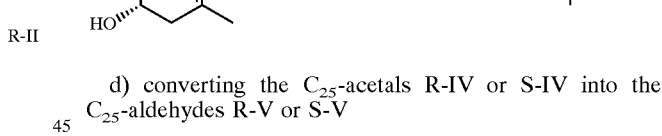
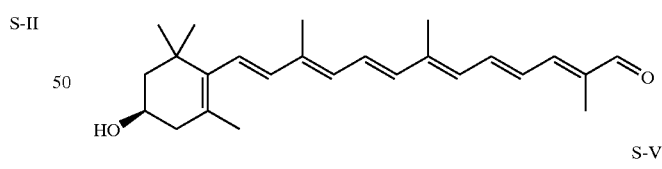

e) and reacting the $C_{25}$-aldehyde R-V with the $C_{15}$-phosphonium salt S-II or the $C_{25}$-aldehyde S-V with the $C_{15}$-phosphonium salt R-II in a Wittig reaction to give sterically uniform meso-Zeaxanthin.

In the case of the $C_{10}$-dial monoacetal III used in process step c), possible open-chain acetals as alkyl radicals $R^1$ and $R^2$ are linear or branched $C_1$–$C_8$-alkyl radicals, e.g. methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl and n-octyl.

Preferred alkyl radicals for $R^1$ and $R^2$ are methyl, ethyl, n-propyl and 1-methylethyl, particularly preferably methyl and ethyl.

For cyclic acetals, possible alkyl radicals for $R^3$ to $R^5$ are linear or branched $C_1$–$C_4$-alkyl radicals, e.g. methyl, ethyl, n-propyl, 1-methylethyl, n-butyl, 1-methylpropyl, 2-methylpropyl and 1,1-dimethylethyl.

Preferred radicals for $R^3$ to $R^5$ are hydrogen and methyl.

The radical Ph of the $C_{15}$-phosphonium salts R-II and S-II designates customary aryl radicals occurring in phosphines and phosphonium salts, such as phenyl, toluene, naphthyl, if appropriate in each case substituted, preferably phenyl.

The radical $X^-$ is an anion equivalent of an inorganic or organic acid, preferably strong inorganic or organic acid.

The expression strong acid includes hydrohalic acids (in particular hydrochloric acid and hydrobromic acid), sulfuric acid, phosphoric acid, sulfonic acids and other inorganic or organic acids having a comparable degree of dissociation. Strong organic acids are to be understood in this connection as also meaning $C_1$–$C_6$-alkanoic acids such as formic acid, acetic acid, propionic acid, butyric acid and caproic acid.

Particularly preferred anions are those of acids selected from the group consisting of hydrochloric acid, hydrobromic acid, sulfuric acid, phosphoric acid, formic acid, acetic acid and sulfonic acid, very particularly preferably $Cl^-$, $Br^-$, $C_nH_{2n+}$—$SO_3^-$ (where n=1–4), Ph-$SO_3^-$, p-Tol-$SO_3^-$ or $CF_3$—$SO_3^-$.

For the preparation of the racemic mixture of the acetylenediols R-I and S-I, oxoisophorone VIII is used as a starting material and is converted into X in a manner known per se by catalytic hydrogenation, for example using Raney nickel in methanol. Racemic IX, which, however, does not have to be isolated, is passed through as an intermediate here. X is obtained as a trans/cis diastereomer mixture, trans-X being the predominant main product. trans-X and cis-X are in each case present as the racemate. The separation of the diastereomers can be carried out according to one of the methods discussed in EP-A-0 775 685, preferably by distillative processes. The racemic cis-X obtained here as a by-product can be equilibrated by base-catalyzed epimerization of $C_6$ to give a mixture of racemic cis-X and racemic trans-x and fed back into the distillative separation of diastereomers. The pure racemic trans-X is converted into the racemic mixture R-I/S-I in 3 stages according to the synthesis indicated in Helv. Chim. Acta. 73 (4), 868, (1990).

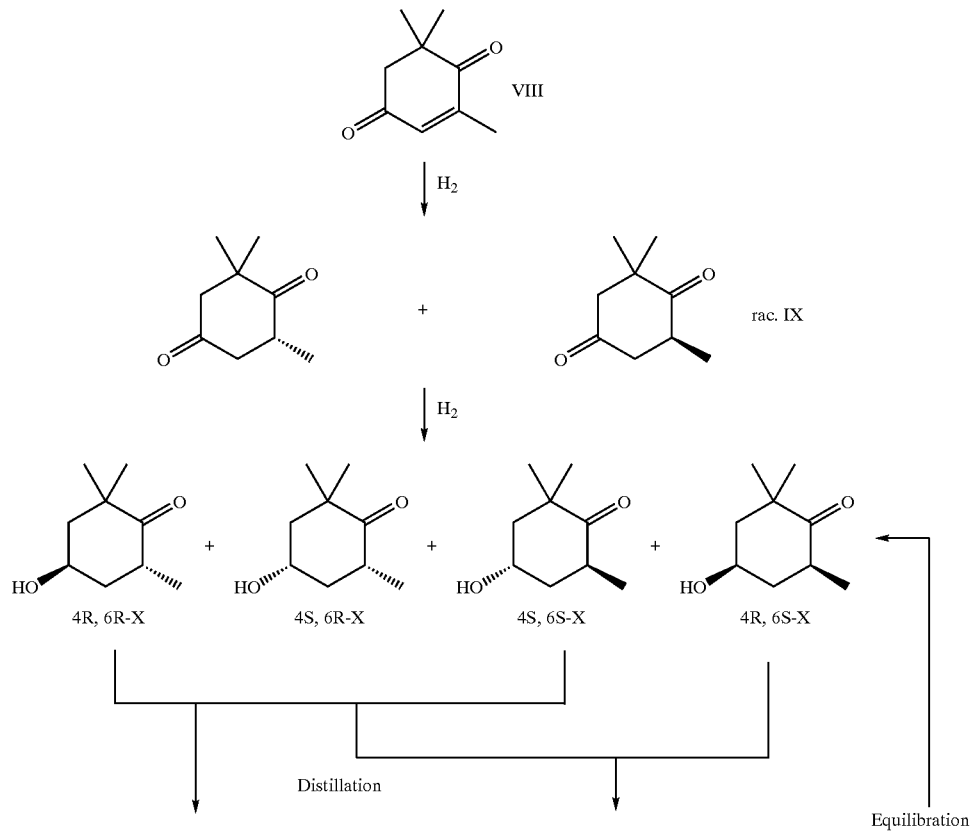

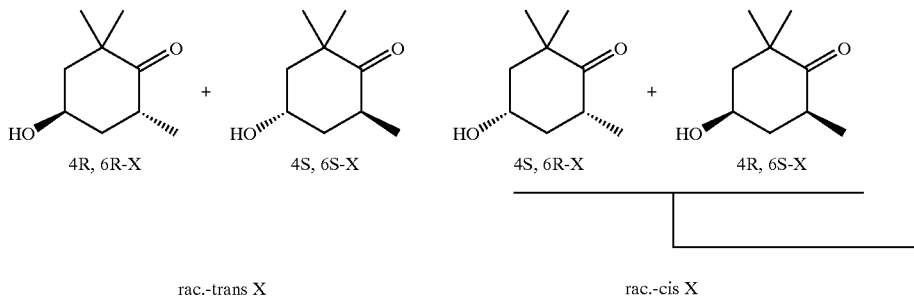

rac.-trans X                rac.-cis X

The process according to the invention is thus also one wherein the mixture employed in stage a) is a diastereomerically pure racemate of the acetylenediols R-I and S-I.

The resolution of the racemic mixture in process step a) can be carried out according to methods known per se, for example by enzymatically catalyzed separation of enantiomers, by chromatography on a chiral column or by separation of diastereomers.

A preferred variant of the process according to the invention comprises converting a racemic mixture of the acetylenediols R-I and S-I in stage a) into a mixture of diastereomers using an optically active auxiliary reagent, separating the diastereomers and subsequently eliminating the auxiliary reagent again.

Thus it has now surprisingly been found that the racemic mixture of the acetylenediols R-I and S-I can be resolved into its antipodes in a particularly simple manner after derivatization using optically active auxiliary reagents to give the diastereomeric intermediates R-VI and S-VI,

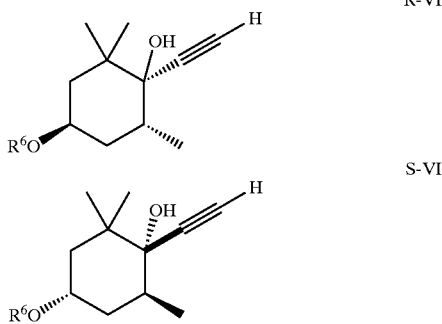

in which the substituent $R^6$ is preferably an optically active urethane, carbonate, sulfonate or acyl radical.

The derivatization takes place completely selectively on the secondary OH group. The acetylenediols R-I and S-I surprisingly prove stable both chemically and also in terms of configuration to the conditions which are necessary for the introduction of the chiral auxiliary group, separation of the diastereomeric intermediates R-VI and S-VI and elimination of the auxiliary group.

Suitable diastereomeric intermediates R-VI and S-VI are in principle all derivatives by means of which racemic alcohols can be cleaved into their antipodes (cf. Houben-Weyl, Methoden der organischen Chemie [Methods of organic chemistry], alcohols, Part III, p. 785 f., 1984).

A preferred embodiment of the process according to the invention comprises derivatizing the racemate selectively on the secondary OH group in process step a) using an optically active auxiliary reagent selected from the group consisting of carboxylic acids, carboxylic acid halides, chlorocarbonic acid esters, sulfonic acids and isocyanates.

The diastereomeric intermediates of the formulae R-VI and S-VI are thus preferably carboxylic acid esters, sulfonic acid esters, carbonates and urethanes, but also monoesters of dicarboxylic acids which for their part can be converted into diastereomeric salts using optically active amines, for example using brucin, ephedrine, quinine, menthylamine or strychnine.

For the preparation of diastereomeric urethanes, a racemic mixture of the acetylenediols R-I and S-I, for example, can be reacted in an inert solvent with isocyanates of optically active amines, such as, for example, (+)- or (−)-phenylethyl isocyanate, (+)- or (−)-1-(1-naphthyl)ethyl isocyanate or (+)- or (−)-menthyl isocyanate.

Carbonates are prepared, for example, by reaction of R-I or S-I with esters of chloroformic acid, preferably with menthyl chloroformate.

For the preparation of diastereomeric carboxylic acid or sulfonic acid esters, the racemic mixture of the acetylenediols R-I and S-I, for example, can be reacted with ω-camphanoic acid, menthyloxy acetic acid, lactic acid, mandelic acid, methyl O,O-diacetyltartrate, α-tosylaminocarboxylic acids, trans-chrysanthemic acid, camphor-10-sulfonic acid or with their acid chlorides.

With respect to industrial feasibility, diastereomeric esters are particularly advantageous, since the chiral auxiliary reagent can be recovered by simple acid/base separation after separation of diastereomers and ester hydrolysis has taken place and fed back into the process.

In addition to the compounds known from Houben-Weyl, alcohols, Part III, p. 785 f. (1984) and already mentioned above are preferably derivatives of D- or L-lactic acid such as, for example, α-chloropropionic acid, α-phenoxypropionic acid and α-phenoxypropionic acids substituted on the phenyl group in any desired manner, particularly preferably D- or L-2,4-dichlorophenoxypropionic acid, very particularly preferably D-2,4-dichlorophenoxypropionic acid or D-2,4-dichlorophenoxypropionyl chloride.

In a preferred embodiment of the process according to the invention, the racemic mixture of the acetylenediols R-I and S-I is reacted with 1–1.2 equivalents of D-2,4-dichloropropionyl chloride at approximately 0° C. to room temperature in an inert solvent in the present of a base. A mixture of the diastereomeric 2,4-dichlorophenoxypropionic acid esters R-VIa and S-VIa is thus obtained in quantitative yield.

A further advantageous embodiment of the process according to the invention comprises separating the diastereomeric intermediates by crystallization in process step a).

The diastereomeric ester R-VIa belonging to the R series can thus be enriched, for example, with a purity of >95 area percent, preferably >97%, by crystallization from the crude 1:1 mixture of diastereomers.

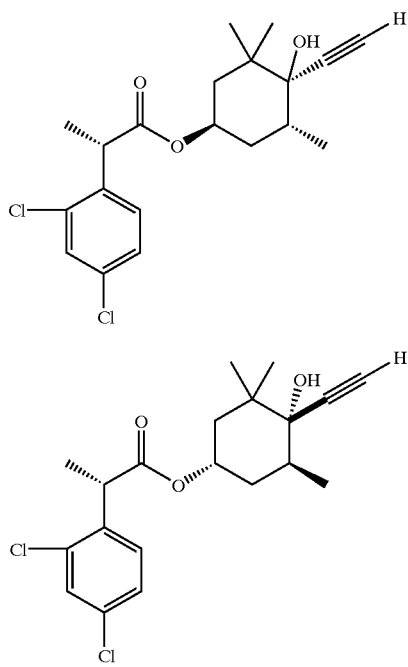

R-VIa

S-VIa

The corresponding diastereomeric ester S-VI is enriched in the mother liquor. This process is particularly advantageously designed such that, after the hydrolysis of the diastereomeric ester, the pure S-I can be obtained after the hydrolysis of the diastereomeric esters in the mother liquor with a purity of >95%, preferably of >97%, particularly preferably of >99%, by repeated crystallization.

It is thus possible to obtain both enantiomers in high purity using a cleavage reagent. Moreover, the racemate can be cleaved virtually completely into the enantiomers by means of suitable crystallization, hydrolysis of mother liquors and reesterifications. By means of this procedure, it is possible to obtain both enantiomers in identical amounts, which is indispensable for an economic or total synthesis of meso-Zeaxanthin.

After the racemate cleavage, both enantiomers R-I and S-I can be converted selectively into the phosphonium salt R-II having the R configuration or the phosphonium salt S-II having the S configuration. The preparation of R-II from 1S, 4R, 6R-I (R-I) is in this case carried out analogously to the synthesis described in Helv. Chim. Acta 73 (4), 868 f. (1990). The same synthesis sequence is disclosed in EP-A-0 283 979 for the preparation of 3R, 3'R-Zeaxanthin.

The process according to the invention for the preparation of meso-zeaxanthin comprises the reaction of the acetylenediol S-I to give the phosphonium salt S-II. This substep, which has hitherto not yet been described, is carried out analogously to the synthesis of R-II—described in Helv. Chim. Acta 73 (4), 868 f. (1990) and EP-A-0 283 979.

A possible synthesis sequence corresponds, for example, to the following reaction scheme:

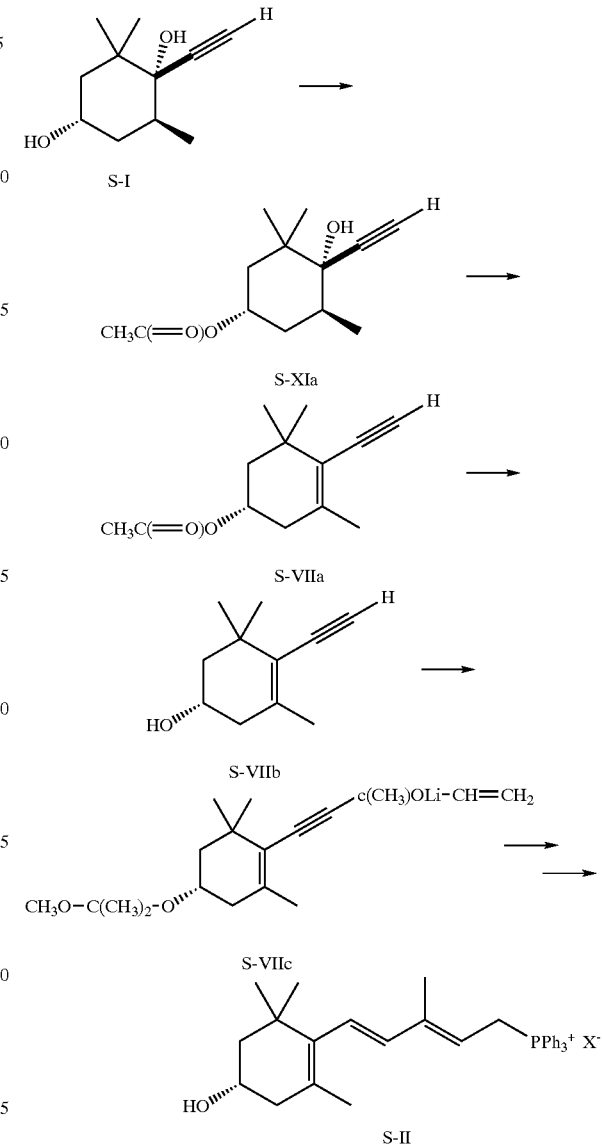

In addition to the abovementioned acetyl protective group, it is possible, of course, also to use other acyl radicals such as, for example, formyl or propionyl radicals. The same applies for the acetal protective group of the compound of the formula S-VIIc. Alternative acetal protective groups are found in the later part of the description.

Details of the individual reactions are found in the literature cited above.

In order to obtain meso-zeaxanthin which is completely free of R,R-zeaxanthin and S,S-zeaxanthin from the phosphonium salts R-II and S-II, the Wittig reactions of the central $C_{10}$ unit with R-II or S-II must proceed completely selectively in succession. The selectivity necessary for the synthesis of a uniform product is only guaranteed if a $C_{10}$-dialdehyde corresponding to the general formula III is employed, in which a carbonyl group is protected as an acetal.

For the process according to the invention, the neopentyl glycol acetal IIIa is preferably employed.

The reaction of the phosphonium salts R-II and S-II with IIIa via the acetals R-IVa and S-IVa to give the aldehydes R-V and S-V is described in Helv. Chim. Acta 64 (7), 2489, 1981. However, hereto the reaction was only carried out on the mmol scale. The aldehydes R-V and S-V were isolated there in a complicated manner by means of combination of chromatography and crystallization. The further reaction to give meso-zeaxanthin is not described in this publication.

A further object thus consisted in finding a process to link the units R-II, S-II and III in an industrially feasible manner. Surprisingly, it was seen that a highly pure meso-zeaxanthin was obtained in excellent yield without purification of the intermediates obtained.

Advantageously, a procedure is used in which R-II or S-II (sequence arbitrary) is reacted with III, preferably with IIIa, under the standard conditions described for Wittig reactions of this type (see Carotenoids, Vol. 2, "Synthesis", p. 79 ff.; Birkhäuser Verlag, 1996, and literature cited there), the use of an oxirane as a latent base being preferred. The crude acetals R-IV and S-IV can be hydrolyzed directly with acidic catalysis to give the aldehydes R-V and S-V. In principle, all conditions for acid-catalyzed cleavage of acetals are suitable here. A preferred embodiment of the acetal cleavage consists, however, in stirring the acetal in aqueous-alcoholic medium with catalytic amounts of citric acid (about 5 to 50 mol %, preferably 20 to 30 mol %) in the temperature range from approximately 0° C. to reflux temperature, preferably at 20 to 30° C.

The crude products of the acetal cleavage, i.e. the crude aldehydes R-V and S-V, are reacted with the phosphonium salts S-II (for R-V) or R-II (for S-V) under the abovementioned conditions of the Wittig reaction. Sterically uniform meso-zeaxanthin is obtained in high yield. Here too, the oxirane variant of the Wittig reaction is preferred, since a product of excellent purity is obtained by direct crystallization from the reaction mixture.

The condensation of R-II or S-II with III can be carried out, for example, in an inert organic solvent, e.g. in open-chain or cyclic ethers such as diethyl ether, diisopropyl ether, methyl tert-butyl ether, 1,4-dioxane or THF, in halogenated hydrocarbons such as dichloromethane, chloroform, in aromatic hydrocarbons such as toluene, xylene or benzene or in polar solvents such as dimethylformamide, dimethyl sulfoxide or acetonitrile.

As base, all bases customary for Wittig condensations can be used, e.g. alkali metal hydroxides such as sodium hydroxide, potassium hydroxide or lithium hydroxide; alkali metal hydrides such as sodium hydride or potassium hydride.

Possible bases are moreover organolithiums such as, for example, n-butyllithium, tert-butyllithium, phenyllithium or alkali metal amides such as lithium, potassium or sodium amide, lithium diisopropylamide but also alkali metal hexamethyl disilacides.

The amount of base employed is as a rule in the range from 0.8 to 5 mol, preferably 1 to 3 mol, per mole of the phosphonium salts II employed.

If $X^-$ is a halide anion, oxiranes can also be advantageously employed as latent bases (see Chem. Ber. 1974, 107, 2050).

Preferably, solutions of alkali metal alkoxides in the corresponding alcohol or oxiranes, especially 1,2-epoxybutane, without additional solvents or as a mixture with one of the abovementioned solvents or a lower alcohol, are used as bases for this Wittig reaction.

It was thus possible to achieve the object of obtaining sterically uniform meso-zeaxanthin of high chemical purity from the phosphonium salts R-II and S-II in an industrially useful manner without purification of intermediates.

The invention likewise relates to a process for the preparation of optically pure acetylenediols of the formulae R-I and S-I,

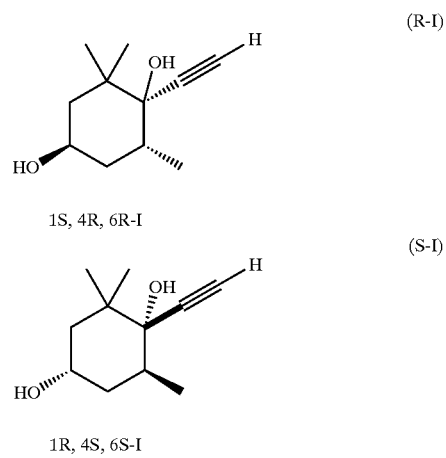

which comprises converting a racemic mixture of the acetylenediols R-I and S-I into a mixture of diastereomers using an optically active auxiliary reagent and resolving this into its antipodes.

The process is one wherein the mixture is a diastereomerically pure racemate.

The process is further one wherein the racemate is derivatized selectively on the secondary OH group using an optically active auxiliary reagent selected from the group consisting of carboxylic acids, carboxylic acid halides, chlorocarboxylic acid esters, sulfonic acids and isocyanates to give a mixture of diastereomeric intermediates of the formulae R-VI and S-VI,

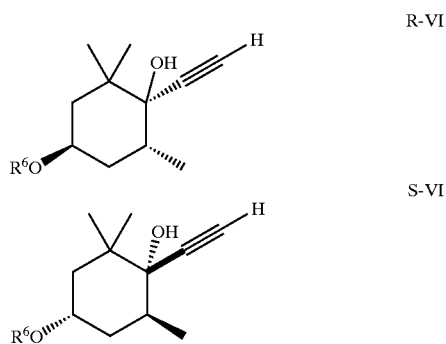

in which the substituent $R^6$ is an optically active urethane radical, carbonate radical, sulfonate radical or an acyl radical.

As optically active auxiliary reagents, D- or L-lactic acid derivatives, particularly preferably D-2,4-dichlorophenoxypropionic acid or D-2,4-dichlorophenoxypropionyl chloride, are preferably employed.

An advantageous embodiment of the process comprises separating the diastereomeric intermediates by crystallization.

The invention also relates to optically active cyclohexane derivatives of the general formulae R-VI and S-VI,

R-VI

S-VI

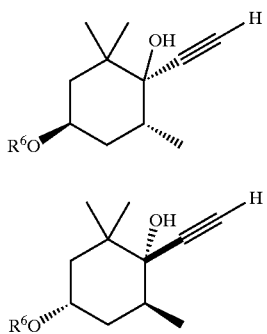

in which the substituent $R^6$ is an optically active urethane radical, carbonate radical, sulfonate radical or an acyl radical.

The invention also relates to 2,4-dichlorophenoxypropionic acid esters of the formulae R-VIa and S-VIa and also R-VIb and S-VIb R-VIa S-VIa R-VIb S-VIb The invention also relates to an optically active acetylenediol of the formula S-I (S-I)

1R, 4S, 6S-I

The invention also relates to optically active acetylene compounds of the general formula S-VII,

S-VII in which the substituents independently of one another have the following meaning:

$R^7$ is hydrogen, $C_1$–$C_{12}$-acyl or a hydrolytically cleavable acetal or ether protective group;

$R^8$ is hydrogen or $C(CH_3)OR^9$—CH=CH$_2$;

$R^9$ is lithium or hydrogen.

Acyl radicals for $R^7$ are understood as meaning branched or unbranched, saturated or unsaturated $C_1$–$C_{12}$-acyl radicals.

Examples of these are acyl radicals of formic, acetic, propionic, n-butyric, isobutyric, sorbic, n-valeric, isovaleric, caproic, caprylic, capric, undecanoic and lauric acid. Acyl radicals of formic, acetic and propionic acid are preferred, particularly preferably acetate.

Hydrolytically cleavable acetal or ether protective groups for $R^9$ are to be understood as meaning protective groups which can be converted by hydrolysis into a hydroxyl group. Mention may be made, for example, of ether groups, such as

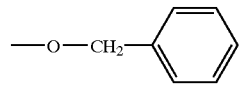

and —O—C(CH$_3$)$_3$, silyl ether groups, such as —O—Si(CH$_3$)$_3$, —O—Si(CH$_2$CH$_3$)$_3$, —O—Si(isopropyl)$_3$, —O—Si(CH$_2$CH$_2$)$_2$(i-propyl), —O—Si(CH$_3$)$_2$(tert-butyl)

and —O—Si(CH$_3$)$_2$(n-hexyl) or substituted methyl ether groups, such as the α-alkoxy or α-aryloxy alkyl ether groups of the formulae

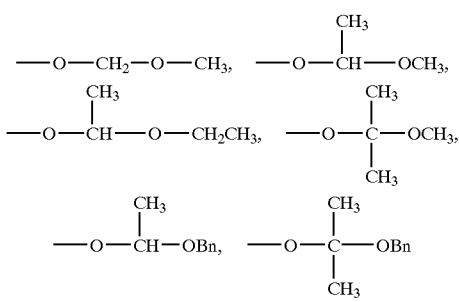

Bn = Benzyl and suitable pyranyl ether groups, such as the tetrahydropyranyloxy group and the 4-methyl-5,6-dihydro-2H-pyranyloxy group.

Preferably, the tetrahydropyranyloxy group

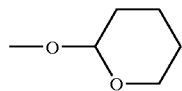

or the α-ethoxyethoxy group of the formula

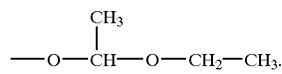

is used for R$^3$.

The appropriate reaction conditions for the introduction and removal of the abovementioned protective groups are found, inter alia, in T. Greene "Protective Groups in Organic Chemistry", John Wiley & Sons, 1981, Chapter 2.

The invention likewise relates to optically active cyclohexane derivatives of the general formula S-XI,

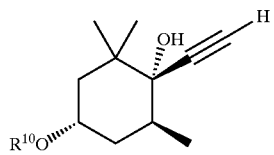

in which R$^{10}$ is a non-chiral C$_1$–C$_{12}$-acyl group or a hydrolytically cleavable acetal or ether protective group. The closer definition of the radicals R$^{10}$—generally and in the preferred embodiment—corresponds to the abovementioned description for R$^7$.

The process according to the invention will be illustrated in greater detail with the aid of the following examples.

EXAMPLE 1a

Racemic 1S,4R,6R-I/1R,4S,6S-I 156.4 g (1.0 mol) of racemic trans-X (purity according to GC: 99.9%) were dissolved in 250 ml of THF. 0.25 g (1 mmol) of pyridinium 4-toluenesulfonate were added and 163.2 g (2.15 mol) of isopropenyl methyl ether (purity according to GC: 95%) were then added dropwise in the course of 45 min. The reaction temperature was kept at approximately 25° C. during the course of this by cooling with a water bath. After completion of the addition of the isopropenyl methyl ether, the mixture was stirred at 25° C. for a further 2 h.

The reaction mixture was subsequently added at 0° C. to a suspension of lithium acetylide in THF in the course of 1 h.

The lithium acetylide suspension was prepared in the following way:

A total of 14.0 g (2.0 mol) of lithium granules were added in portions at –40° C. in the course of 1 hour to 750 ml of liquid ammonia. The liquid was subsequently treated with 150 l of acetylene at –40° C. in the course of 3 h. 750 ml of THF were added at –40° C. and the temperature was then slowly allowed to rise to 0° C. in the course of 90 min, the mixture being treated further with acetylene (50 l/h).

After addition of the acetylization solution of rac-trans-X, the mixture was stirred at 0° C. for 1 hour. 400 ml of ice water were then added dropwise at 0° C. in the course of 1 hour. The mixture was allowed to come to room temperature. After adding 700 ml of hexane, the aqueous lower phase was separated off and reextracted twice with 700 ml of hexane each time. The combined organic phases were washed once with 700 ml of semiconcentrated ammonium chloride solution and semiconcentrated sodium chloride solution in each case, dried over sodium sulfate and concentrated on a rotary evaporator. The residue (287 g, pale-yellow solid) was dissolved in 1 300 ml of THF. 52 ml of water and 2.51 g of pyridinium 4-toluenesulfonate were added and the mixture was stirred at room temperature for 1 hour. It was then diluted with 700 ml of ethyl acetate and washed with 500 ml of saturated ammonium chloride solution. The organic phase was subsequently washed with 500 ml of saturated sodium chloride solution. The combined water phases were reextracted twice with 250 ml of ethyl acetate each time. The combined organic phases were dried over sodium sulfate and concentrated on a rotary evaporator. The residue was crystallized from a mixture of 250 ml of ethyl acetate and 750 ml of diisopropyl ether. 124 g of first crystallizates having a yield of 68.1% were obtained, based on rac-trans-X. Purity according to GC: 98.9%; m.p.: 124.5 to 125° C.

The filtrate was concentrated to about 300 ml. The mixture was stirred at 0° C. for 1 h and the second crystallizate was filtered off. Final weight of second crystallizate: 23 g; yield: 12.6% based on rac-trans-X; purity according to GC: 98.4%; m.p.: 124 to 124.5° C.

EXAMPLE 1b

Conversion of 1S,4R,6R-I/1R,4S,6S-I into the diastereomeric D-2,4-dichlorophenoxypropionic acid esters R-VIa and S-VIa 182 g (1.0 mol) of crystalline R-I/S-I were dissolved in a mixture of 95 g (1.1 mol) of pyridine and 2 000 ml of methyl tert-butyl ether. 290 g (1.1 mol) of D-2,4-dichlorophenoxypropionyl chloride (purity according to GC: 96.2%) were metered in at 0 to 5° C. in the course of 1 h and the reaction batch was stirred at this temperature for 1 hour. After subsequent addition of 300 ml of water, the aqueous lower phase was separated off. The organic upper phase was washed once with 150 ml each of 5% strength sulfuric acid, water, saturated bicarbonate solution and water again, dried over sodium sulfate and concentrated on a rotary evaporator.

In four similar batches, the following final weights were obtained:

| Batch | Final weight of diastereomeric esters | GC content (area %) |
|---|---|---|
| 1 | 421.3 g | 97.9% |
| 2 | 418.3 g | 98.4% |
| 3 | 425.3 g | 98.3% |
| 4 | 424.0 g | 98.8% |

EXAMPLE 1c

Separation of diastereomers 840 g each of the diastereomeric esters obtained in Example 1b were crystallized from a mixture of 2 000 ml of hexane and 200 ml of diisopropyl ether in two batches. The crystallizates of both batches and the mother liquors of both batches were combined.

The total final weight of crystallizate was 575.2 g, the amount of mother liquor evaporation residue was 1 142 g.

Composition according to GC analysis (area %):

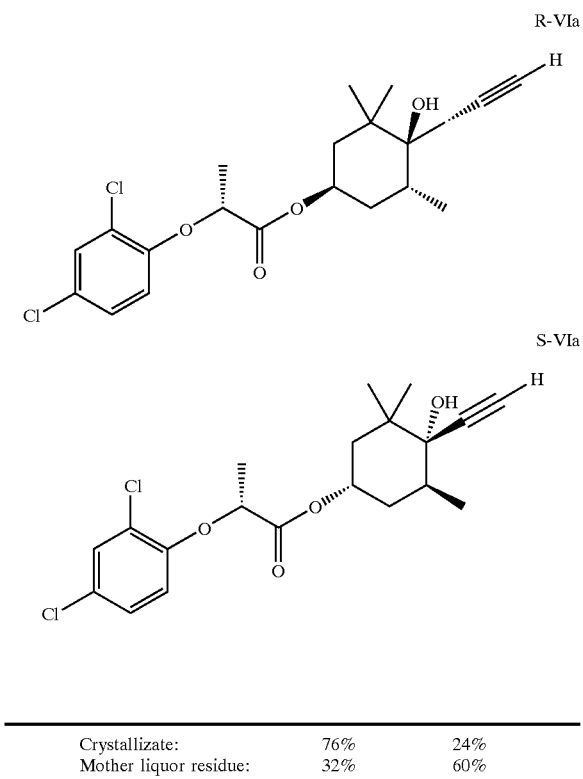

R-VIa

S-VIa

| | | |
|---|---|---|
| Crystallizate: | 76% | 24% |
| Mother liquor residue: | 32% | 60% |

EXAMPLE 1d

High purification of R-VIa

The crystallizate from Example 1c (575 g) was dissolved in 350 ml of diisopropyl ether at 50° C. After addition of 1 725 ml of n-hexane, the reaction batch was cooled to room temperature and stirred overnight. The crystallizate was filtered off and dried in a stream of nitrogen. Final weight of crystallizate: 372 g; composition according to GC: 89.9% of R-VIa, 10.4% of S-VIa.

The filtrate was concentrated on a rotary evaporator. Final weight of mother liquor residue: 190.9 g; composition according to GC: 42.6% of R-VIa, 56.5% of S-VIa.

The crystallizate (372 g) was recrystallized again from 225 ml of diisopropyl ether and 1 120 ml of n-hexane. Final weight: 305.2 g; m.p.: 84.5 to 85° C., purity according to GC: >97% of R-VIa; specific rotation (D 25° C.): +9.74° (c=1 in methyl tert-butyl ether).

The filtrate was concentrated on a rotary evaporator. Final weight of mother liquor residue: 67.2 g; composition according to GC: 59.2% of R-VIa, 40.8% of S-VIa.

The combined mother liquor residues (258 g) contained the diastereomeric esters R-VIa and S-VIa approximately in the ratio 1:1 and no other secondary components in addition. It was possible to feed them back directly into the separation of diastereomers according to Example 1c.

EXAMPLE 1e

Hydrolysis of the diastereomeric ester R-VIa 300.0 g (0.75 mol) of the compound R-VIa from Example 1d were dissolved in 1.5 l of methanol. A solution of 110 g of potassium hydroxide in 1.5 l of methanol was allowed to run in at room temperature and the mixture was stirred at room temperature overnight. 990 g of 10% strength acetic acid solution were subsequently added and the reaction mixture was concentrated on a rotary evaporator after a stirring time of a few minutes. 0.5 l of saturated sodium chloride solution was added to the residue and the mixture was then extracted once with 750 ml and three times with 250 ml each of methyl tert-butyl ether. The combined organic phases were washed three times with 400 ml each of saturated bicarbonate solution and once with 200 ml of water, dried over sodium sulfate and concentrated on a rotary evaporator.

The evaporation residue was dissolved in 200 ml of ethyl acetate in the presence of heat. 450 ml of diisopropyl ether were added and the reaction batch was then allowed to stand at 5° C. overnight. The crystallizate was filtered off and dried in a stream of nitrogen. Final weight: 116.9 g, R-I; yield: 85.6% of theory; m.p.: 150 to 150.5° C.; purity according to GC: 98.5% of R-I (25 m Chirasil-Dex.); specific rotation (D, 25° C.): −28.39° (c=1 in methanol).

The crystallizate was converted into the $C_{15}$-phosphonium salt R-II having the R configuration according to the details in the literature (Helv. Chim. Acta 73, 868 (1990) and EP 283979.

EXAMPLE 1f

Hydrolysis of the mother liquor residue from Example 1c enriched in diastereomeric ester S-VIa The mother liquid residue from Example 1c was processed further in two identical batches as follows: 533 g (1.335 mol) in each case were dissolved in 2.7 l of methanol and treated at room temperature with a solution of 194 g of potassium hydroxide in 2.7 l of methanol. After stirring for a number of hours, 1.77 kg of 10% strength acetic acid were added and the mixture was briefly stirred again. Both batches were combined and concentrated on a rotary evaporator at a bath temperature of 50° C. The residue was treated with 1 870 ml of saturated sodium chloride solution and extracted once with 2.7 l and three times with 800 ml each of methyl tert-butyl ether. The combined organic phases were washed five times with 1.3 l each of saturated bicarbonate solution and once with 700 ml of water, dried over sodium sulfate and concentrated in a rotary evaporator. Final weight: 355 g; GC analysis (25 m Chirasil-Dex): 57.8% of (1R,4S,6S)-I (S-I), 34.7% of (1S,4R,6R)-I (R-I).

The combined water phases were concentrated to approximately half the volume on a rotary evaporator. The resulting precipitate was filtered off and taken up with 2 l of methyl tert-butyl ether and 1.5 l of water. The organic phase was washed with 500 ml of water. The two aqueous phases were combined and reextracted twice with 500 ml each of methyl tert-butyl ether. The combined organic phases were dried over sodium sulfate and concentrated on a rotary evaporator.

Both evaporation residues were combined for the high purification (see Example Ii). Final weight: 63.4 g; GC analysis (25 m Chirasil-Dex): 82.7% of S-I, 17.2% of R-I.

EXAMPLE 1g

Recovery of the D-2,4-dichlorophenoxypropionic acid

The combined water phases from Example 1f were concentrated to about half the original volume on a rotary evaporator. The concentrate was adjusted to pH 1 by dropwise addition of 97% strength sulfuric acid at room temperature. The mixture was subsequently stirred for 30 min and the solid was filtered off. The filtercake was washed three times with 1 l each of water and dried at 50° C./10 mbar. Final weight: 565 g; yield: 90.0%; m.p.: 110 to 115° C.; purity according to GC: 97.8%.

For the high purification, this material was recrystallized from 3 l of toluene. m.p.: 122 to 122.5° C.; specific rotation (D, 25° C.): +40.02° (c=1 in methyl tert-butyl ether).

EXAMPLE 1h

Preparation of D-2,4-dichlorophenoxypropionyl chloride 235 g (1.0 mol) of D-2,4-dichlorophenoxypropionic acid were introduced. 179 g (1.5 mol) of thionyl chloride were allowed to run in and the mixture was warmed slowly to 100° C. in the course of 3 h. It was subsequently stirred at 100° C. for 1 h and excess thionyl chloride was then stripped off at 100° C./20 mbar. The residue was purified by means of a distillation bridge. 245.8 g of D-2,4-dichlorophenoxypropionyl chloride passed over at 130° C./60 mbar. Yield: 96.7% of theory; purity according to GC: 100%; specific rotation (D, 25° C.): +33.23° (c=1 in n-hexane).

EXAMPLE 1i

High purification of S-I 417 g of purified evaporation residue from Example 1f were dissolved in 730 ml of ethyl acetate in the presence of heat. 1 460 ml of diisopropyl ether were added and a hot filtration was carried out. The filtrate was allowed to come to room temperature and was subsequently stirred overnight. The crystallizate was filtered off with suction and dried in a stream of nitrogen. Final weight of crystallizate 1:246.6 g; GC analysis (25 m Chirasil-Dex): 72.8% of S-I, 25.3% of R-I.

The filtrate was concentrated on a rotary evaporator. The final weight of mother liquor 1:167.9 g; GC analysis (25 m Chirasil-Dex): 43.5% of S-I, 46.8% of R-I.

The crystallizate 1 was taken up in 450 ml of ethyl acetate in the presence of heat and, after addition of 900 ml of diisopropyl ether, crystallized as above. Final weight of crystallizate 2: 175.9 g; GC analysis (25 m Chirasil-Dex): 86.9% of S-I, 12.8% of R-I.

The filtrate was concentrated on a rotary evaporator. Final weight of mother liquor 2: 70.1 g; GC analysis (25 m Chirasil-Dex): 48.3% of S-I, 51.3% of R-I.

The crystallizate 2 was again recrystallized from 300 ml of ethyl ester and 630 ml of diisopropyl ether as described above. In this process, an optically pure 1R,4S,6S-I was obtained as crystallizate 3. Final weight of crystallizate 3:130.8 g; m.p.: 150.5 to 151° C.; GC analysis (25 m Chirasil-Dex): 99.3% of S-I (the enantiomer R-I was not detected); specific rotation (D, 25° C.): +28.32 ° (c=1 in methanol).

The filtrate was concentrated on a rotary evaporator. Final weight of mother liquor 3: 44.9 g; GC analysis (25 m Chirasil-Dex): 53.6% of S-I, 45.8% of R-I.

The mother liquor residues 1 to 3 were combined (282.9 g). They contained the two enantiomers S-I and R-I approximately in the ratio 1:1. It was possible to feed them back directly into derivatization to give the diastereomeric D-2,4-dichlorophenoxypropionic acid esters according to Example 1b.

EXAMPLE 1j (1R,4S,6S)-$C_{11}$-Monoacetate S-XIa

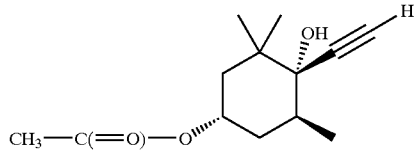

242.4 g (1.33 mol) of S-I were dissolved in 463 g (5.85 mol) of pyridine. The mixture was cooled to 0° C. and 543 g (5.32 mol) of acetic anhydride were allowed to run in in the course of 30 min. The mixture was allowed to come to room temperature and was then subsequently stirred at 50° C. for 4 h.

For work-up, the reaction mixture was concentrated on a rotary evaporator. The residue was dissolved in 1.3 l of methylene chloride. The resulting solution was washed once each with 650 ml of 5% strength hydrochloric acid, 330 ml of saturated sodium solution and 330 ml of saturated bicarbonate solution. The combined aqueous phases were reextracted twice with 130 ml each of methylene chloride. The combined organic phases were dried over sodium sulfate and concentrated on a rotary evaporator. The residue (334 g) was taken up using 3 l of hexane and treated at about 50° C. with 15 g of active carbon. After clarifying filtration, the mixture was allowed to cool to ambient temperature and subsequently stirred in an ice-water bath for 1 h. The crystallizate was filtered off with suction, washed with cold n-hexane and dried in a stream of nitrogen. Final weight: 246.1 g; yield: 82.6% of theory; m.p.: 69° C.; purity according to GC: 100%; specific rotation (D, 25° C.): +23.14° (c=1 in EtOH).

The mother liquor was concentrated on a rotary evaporator. By crystallization of the evaporation residue (49.7 g) from 200 ml of n-hexane, the following second crystallizate was obtained: final weight: 40.3 g; yield: 13.5% of theory; m.p.: 68 to 68.5° C.; purity according to GC: 99.44%; specific rotation (D 25° C.): +23.09° (c=1 in EtOH). Total final weight: 286.4 g; total yield: 96.1% of theory.

EXAMPLE 1k $C_{11}$-Acetate S-VIIa

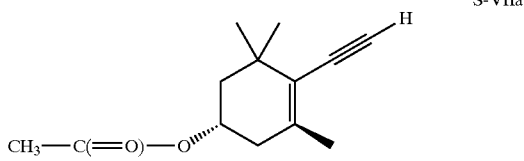

142.4 g (635 mmol) of S-XIa were dissolved in 1.3 l of ortho-xylene. 15.89 g (63.5 mmol) of copper(II) sulfate pentahydrate were added, the mixture was heated to reflux and water was removed from circulation for 2 h. The mixture was then allowed to cool to 90° C., a further 15.85 g (63.5 mmol) of copper(II) sulfate pentahydrate were added and water was removed from circulation for a further 4 h.

Two similar batches were combined and subjected to clarifying filtration through Celite. The filtercake was washed twice with 500 ml each of hexane. The combined filtrates were washed twice with 500 ml each of water and twice with 500 ml of semiconcentrated bicarbonate solution, dried over sodium sulfate and concentrated on a rotary evaporator. The residue (342 g) was purified by vacuum distillation through a 10 cm Vigreux column. 236.4 g (90.4% of theory) of S-VIIa having a purity of 99.1% according to GC distilled over at a passing-over temperature of 9.5 mbar/105–107° C. Specific rotation (D, 25° C.): +68.04° (c=1 in EtOH).

EXAMPLE 1l $C_{11}$-Acetylene alcohol S-VIIb

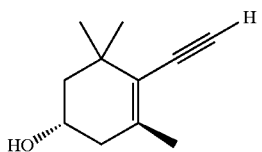

235.6 g (1.14 mol) of S-VIIa were dissolved in 1.1 l of methanol. 93.2 g of potassium hydroxide were introduced in portions at 5° C. to 10° C. in the course of 30 min. The temperature was allowed to come to room temperature and the mixture was subsequently stirred for 30 min. The reaction mixture was then poured onto a mixture of 2.3 l of water and 34 g of acetic acid and extracted three times with 600 ml each of methylene chloride. The combined organic phases were washed once each with 600 ml of saturated sodium chloride solution and 700 ml of saturated bicarbonate solution, dried over sodium sulfate and concentrated on a rotary evaporator. The residue (189 g) was taken up in 1 l of n-hexane in the presence of heat and decolorized with 5 g of active carbon. After removal of the active carbon, the solution was cooled to 5° C. and stirred in an ice-water bath for 1 h. The crystallizate was filtered off and blown dry in a stream of nitrogen. Final weight: 176.3 g; yield: 94.3% of theory; m.p.: 75 to 75.5° C.; specific rotation (D, 25° C.): +129° (c=1 in ethanol); purity according to GC: 99.94%.

5.5 g (2.9% of theory) of second crystallizates were obtained from the mother liquor residue (11 g) by crystallization from n-hexane. m.p.: 70 to 71° C.; specific rotation (D, 25° C.): +121.2° (c=1 in ethanol); purity according GC: 94.93%.

EXAMPLE 1m $C_{15}$-Phosphonium salt S-II 90.33 g (0.55 mol) of $C_{11}$-acetylene alcohol S-VIIb were dissolved in 550 ml of THF. 1.38 g (5.5 mmol) of pyridinium tosylate were added. 99.2 g (1.38 mol) of freshly distilled isopropenyl methyl ether were added dropwise at 20° C. in the course of 30 min. The mixture was subsequently stirred at ambient temperature for 1 h.

The solution of the acetal thus obtained was then cooled to –20° C. 282 g of a 15% strength solution of n-butyllithium in hexane (=0.66 mol of n-butyllithium) were allowed to run in at –10° C. to –15° C. in the course of 30 min. The mixture was subsequently stirred at –15° C. for 15 min and a solution of 47.76 g (0.55 mol) of lithium bromide in 410 ml of THF was then added dropwise at –10° C. in the course of 30 min. The mixture was stirred at –10° C. for 10 min and 57.8 g (0.825 mol) of freshly distilled 1-buten-2-one were then added at –10° C. in the course of 30 min. The mixture was subsequently stirred at –10° C. for 45 min. 191 g of a 70% strength toluene solution of sodium dihydrobis(2-methoxyethoxy)aluminate were then added dropwise at this temperature in the course of 30 min. After dropwise addition was complete, the mixture was subsequently stirred at –10° C. for 10 min. It was allowed to warm to 0° C. and was subsequently stirred at 0° C. for 1 h.

For work-up, a mixture of n-hexane/ethanol [80/40 (v/v)] was allowed to run in at 0° C. 825 ml of 28% strength sodium hydroxide solution were subsequently added at 0° C. The mixture was subsequently stirred at 0° C. for 15 min and the organic upper phase was then separated off. The aqueous lower phase was reextracted three times with 500 ml each of n-hexane. The combined organic phases were washed with 350 ml of saturated sodium solution, dried over sodium sulfate and concentrated on a rotary evaporator. The residue was dried at 50° C.

The following final weights were obtained from two similar batches:

Batch A: 170 g
Batch B: 173 g 349.7 g (1.32 mol) of triphenylphosphine were suspended in 1.1 l of methanol. 137 g of 37% strength hydrochloric acid were added dropwise at 0° C. and the mixture was subsequently stirred at 0° C. for 15 min. A solution of the combined evaporation residues from batch A and batch B (343 g) in 350 ml of methanol was then added dropwise to this at 0° C. The mixture was subsequently stirred overnight at room temperature.

For work-up, it was treated with 550 ml of water and 1.3 l of n-hexane. The aqueous lower phase was separated off and washed three times with 1.3 l each of n-hexene. The combined hexane phases were discarded. The aqueous lower phase was diluted with 900 ml of water and subsequently stirred at room temperature for 30 min with 45 g of active carbon. The active carbon was filtered off and washed with 200 ml of water. The filtrate was concentrated to a total volume of about 1.8 l on a rotary evaporator. The concentrate was extracted three times with 1.5 l each of methylene chloride; the combined organic phases were washed twice with 700 ml each of saturated sodium chloride solution, dried over sodium sulfate and concentrated on a rotary evaporator. The residue was dissolved in 1.1 l of acetonitrile in the presence of heat. After addition of 2.2 l of ethyl acetate, the mixture was cooled to 5° C. The crystallizate was filtered off and dried in vacuo at 50° C. Final weight: 395 g of S-phosphonium salt S-II; yield: 70.5% of theory with respect to S-VIIb; m.p.: 194 to 195° C.; purity according to HPLC: 98.1%; specific rotation (D, 25° C.): +56.180 (c=1 in CH$_2$Cl$_2$) literature value for R-II: −57.2° (c=1 in CHCl$_3$), Helv. Chim. Acta 73, 868 (1990)

After evaporating the mother liquor, a residue of 148 g was obtained. By repeated crystallization from acetonitrile/ethyl acetate, a second crystallizate of 45.1 g (7.9% of theory with respect to S-XII) was obtained. m.p.: 196 to 197° C.; specific rotation (D, 25° C.): +52.38° (c=1 in CH$_2$Cl$_2$); purity according to HPLC: 93.1%.

EXAMPLE 1n

Meso-Zeaxanthin 53.2 g (103 mol) of phosphonium salt R-II (specific rotation (D) −54.79° (c=1 in CH$_2$Cl$_2$) were dissolved in 250 ml of ethanol. 25.0 g (100 mmol) of C$_{10}$-dialdehyde mononeopentyl glycol acetal IIIa and 75 ml of 1,2-epoxybutane were added. The mixture was subsequently stirred under reflux for 20 h. It was allowed to cool to room temperature and concentrated at 50° C. in vacuo on a rotary evaporator. The residue (80.3 g) was dissolved in 300 ml of ethanol. A solution of 4.2 g (20 mmol) of citric acid monohydrate in 70 ml of water was added and the mixture was subsequently stirred at room temperature. For completion of the acetal cleavage, a further 420 mg (2.0 mmol) of citric acid monohydrate in 70 ml of water were added after 1 hour and the mixture was subsequently stirred at room temperature for 1 h. The reaction mixture was then diluted with 1 000 ml of hexane and 500 ml of ethyl acetate. It was washed twice with 100 ml each of saturate bicarbonate solution and once with 100 ml of saturated sodium chloride solution. The combined wash-water phases were reextracted twice with 200 ml each of a 1:1 mixture of hexane/ethyl acetate.

The two organic phases were combined and washed once with 50 ml of saturated sodium chloride solution.

The total combined organic phases were dried over sodium sulfate and evaporated on a rotary evaporator at 50° C.

The evaporation residue (70.5 g) was dissolved in 250 ml of ethanol. 75 ml of 1,2-epoxybutane and 53.26 g (103 mmol) of phosphonium salt S-II (specific rotation (D, 25° C.): +56.18° (c=1 in CH$_2$Cl$_2$) were added. The mixture was subsequently stirred under reflux for 20 h. The resulting suspension was cooled to −10° C. and subsequently stirred at −10° C. for 1 h. The crystallizate was filtered off, washed four times with 100 ml each of ethanol and dried in vacuo at 50° C. Final weight: 44.6 g of meso-zeaxanthin; yield: 79% of theory with respect to C$_{10}$-dial neopentyl glycol acetal; m.p.: 207.5 to 208° C.; purity according to UV: 100%; purity to HPLC: 98%; steric uniformity: >99% meso-zeaxanthin; content of R,R-zeaxanthin and S,S-zeaxanthin in each case <0.3% [HPLC determination according to J. High. Res. Chromatogr. Chrom. Commun. 6, 612 (1989)].

We claim:

1. A process for the preparation of meso-zeaxanthin,

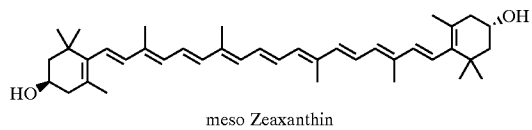

meso Zeaxanthin which comprises a) resolving a racemic mixture of the acetylenediols R-I and S-I

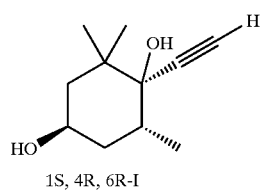

1S, 4R, 6R-I

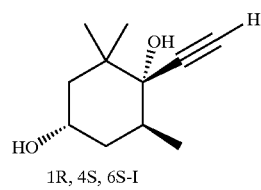

1R, 4S, 6S-I into its antipodes, b) converting the separated antipodes R-I and S-I in each case into the C$_{15}$-phosphonium salts R-II and S-II respectively

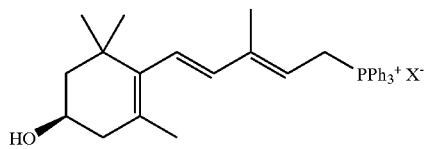

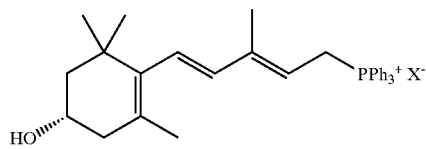

in which Ph is aryl and X is an anion equivalent of an inorganic or organic acid, c) reacting the phosphonium salts R-II or S-II with a C$_{10}$-dial monoacetal of the general formula III,

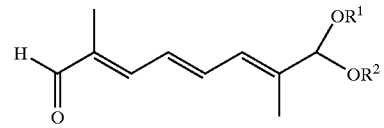

in which the substituents R$^1$ and R$^2$ independently of one another are C$_1$–C$_8$-alkyl or, together with the oxygen atoms and the carbon atom to which they are bonded, can form a 1,3-dioxolane or 1,3-dioxane ring of the following structures

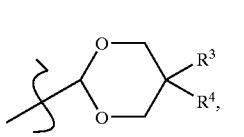 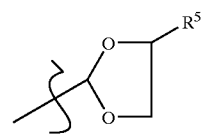

in which R$^3$ and R$^4$ and also R$^5$ in each case independently of one another can be hydrogen or C$_1$–C$_4$-alkyl, in a Wittig reaction to give the C$_{25}$-acetals R-IV or S-IV,

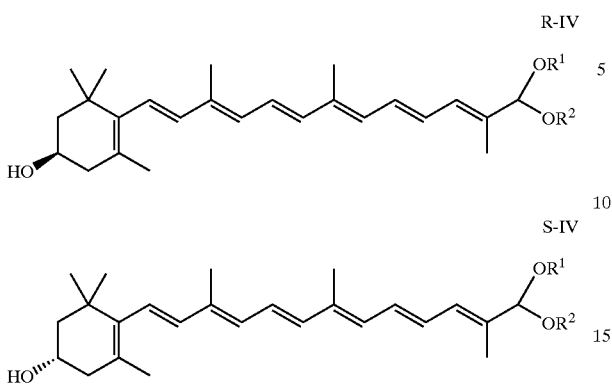

R-IV

S-IV d) converting the $C_{25}$-acetals R-IV or S-IV into the $C_{25}$-aldehydes R-V or S-V

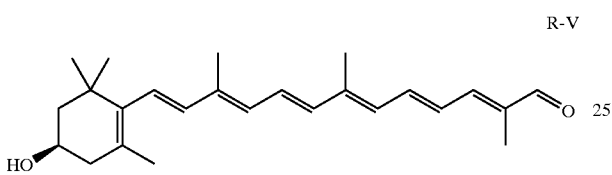

R-V e) and reacting the $C_{25}$-aldehyde R-V with the $C_{15}$-phosphonium salt S-II or the $C_{25}$-aldehyde S-V with the $C_{15}$-phosphonium salt R-II in a Wittig reaction to give sterically uniform meso-zeaxanthin.

2. A process as claimed in claim 1, wherein, in step a), a racemic mixture of the acetylenediols R-I and S-I is converted into a diastereomeric mixture using an optically active auxiliary reagent, the diastereomers are separated and the auxiliary reagent is subsequently removed again.

3. A process as claimed in claim 1, wherein the mixture employed in step a) is a diastereomerically pure racemate of the acetylenediols R-I and S-I.

4. A process as claimed in claim 1, wherein, in process step a), the racemate is derivatized selectively on the secondary OH group using an optically active auxiliary reagent, selected from the group consisting of carboxylic acids, carboxylic acid halides, chlorocarboxylic acid esters, sulfonic acids and isocyanates to give a mixture of diastereomeric intermediates of the formulae R-VI and S-VI,

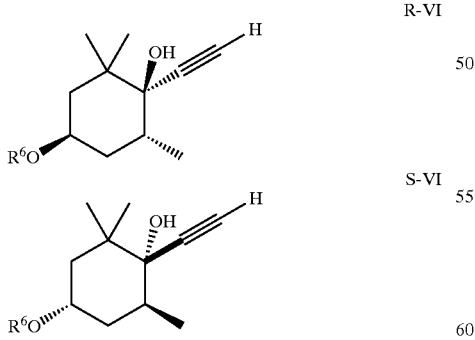

R-VI

S-VI in which the substituent $R^6$ is an optically active urethane radical, carbonate radical, sulfonate radical or an acyl radical.

5. A process as claimed in claim 4, wherein the optically active auxiliary reagents employed are D- or L-lactic acid derivatives.

6. A process as claimed in claim 5, wherein the optically active auxiliary reagent employed is D-2,4-dichlorophenoxypropionic acid or D-2,4-dichlorophenoxypropionyl chloride.

7. A process as claimed in claim 1, wherein, in process step a), the diastereomeric intermediates are separated by crystallization.

8. A process as claimed in claim 6, wherein enantiomerically pure R-I is obtained from the mixture of the diastereomeric D-2,4-dichlorophenoxypropionic acid esters R-VIa and S-VIa

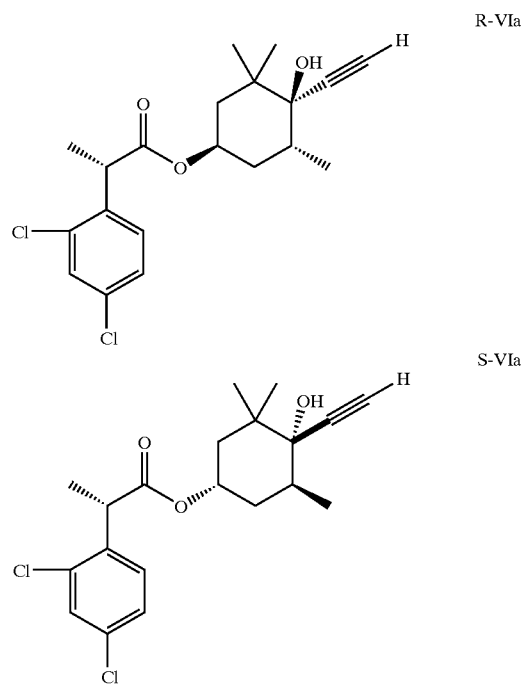

R-VIa

S-VIa by crystallization of the ester and enantiomerically pure S-I is obtained by crystallization of the hydrolyzed alcohol.

9. A process as claimed in claim 1, wherein in process step c) the phosphonium salts R-II or S-II are reacted with a C10-dialdehyde neopentyl glycol monoacetal of the formula IIIa.

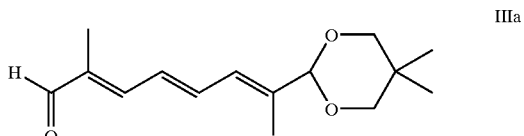

IIIa

10. A process as claimed in claim 1, wherein the acetal cleavage in process step d) is carried out in aqueous-ethanolic medium with addition of citric acid as acidic catalyst.

11. A process as claimed in claim 1, wherein the process steps c) to e) are carried out without purification of an intermediate.

12. A process for the preparation of optically pure acetylenediols of the formulae R-I and S-I, (R-I)

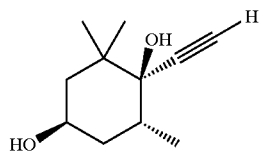

1S, 4R, 6R-I (S-I)

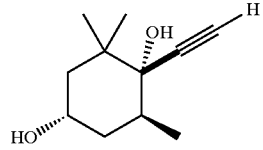

1R, 4S, 6S-I which comprises converting a racemic mixture of the acetylenediols R-I and S-I into a diastereomer mixture using an optically active auxiliary reagent, separating the diastereomers and then removing the auxiliary reagent again.

13. The process as claimed in claim 12, wherein the mixture is a diastereomerically pure racemate.

14. A process as claimed in claim 12, wherein the racemate is derivatized selectively on the secondary OH group using an optically active auxiliary reagent selected from the group consisting of carboxylic acids, carboxylic acid halides, chlorocarboxylic acid esters, sulfonic acids and isocyanates to give a mixture of diastereomeric intermediates of the formulae R-VI and S-VI,

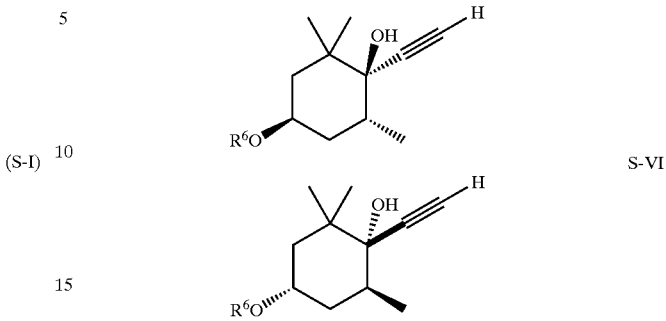

in which the substituent $R^6$ is an optically active urethane radical, carbonate radical, sulfonate radical or an acyl radical.

15. A process as claimed in claim 14, wherein the optically active auxiliary reagent employed is a D- or L-lactic acid derivative.

16. A process as claimed in claim 15, wherein the optically active auxiliary reagent employed is D-2,4-dichlorophenoxypropionic acid or D-2,4-dichlorophenoxypropionyl chloride.

17. A process as claimed in claim 12, wherein the diastereomeric intermediates are separated by crystallization.

* * * * *